United States Patent
Wolff et al.

(10) Patent No.: US 6,881,576 B2
(45) Date of Patent: *Apr. 19, 2005

(54) FORMATION OF POLYAMPHOLYTES IN THE PRESENCE OF A POLYION

(75) Inventors: Jon A. Wolff, Madison, WI (US); James E. Hagstrom, Middleton, WI (US); Vladimir G. Budker, Middleton, WI (US); Vladimir S. Trubetskoy, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 134 days.

This patent is subject to a terminal disclaimer.

(21) Appl. No.: 10/095,752

(22) Filed: Mar. 11, 2002

(65) Prior Publication Data

US 2002/0160515 A1 Oct. 31, 2002

Related U.S. Application Data

(63) Continuation-in-part of application No. 09/753,990, filed on Jan. 2, 2001, now Pat. No. 6,383,811.

(60) Provisional application No. 60/174,132, filed on Dec. 31, 1999.

(51) Int. Cl.$^7$ .......................... C12N 15/64; C12N 15/88
(52) U.S. Cl. ....................... 435/458; 435/456; 435/472; 424/450
(58) Field of Search .......................... 424/450; 435/458, 435/456, 472

(56) References Cited

U.S. PATENT DOCUMENTS 6,126,964 A * 10/2000 Wolff et al. ................. 424/450
6,383,811 B1 * 5/2002 Wolff et al. ................. 435/450

* cited by examiner

*Primary Examiner*—James Ketter
(74) *Attorney, Agent, or Firm*—Mark K. Johnson

(57) ABSTRACT

A polyampholyte is utilized in a condensed polynucleotide complex for purposes of nucleic acid delivery to a cell. The complex can be formed with an appropriate amount of positive and/or negative charge such that the resulting complex can be delivered to the extravascular space and may be further delivered to a cell.

16 Claims, 2 Drawing Sheets

FORMATION OF POLYAMPHOLYTES IN THE PRESENCE OF A POLYION

This application is a Continuation-In-Part of Ser. No. 09/753,990 filed on Jan. 2, 2001 now U.S. Pat. No. 6,383,811 which claims the benefit of Provisional Application No. 60/174,132, filed Dec. 31, 1999.

FIELD

In this specification we describe forming a polyampholyte in the presence of polyion. The polyampholyte is useful in delivering a polyion to a cell. More specifically, the polyion may be a nucleic acid in a preferred embodiment.

BACKGROUND

Low molecular weight cations with valency, i.e. charge, <+3 fail to condense DNA in aqueous solutions under normal conditions. However, cationic molecules with the charge <+3 can be polymerized in the presence of DNA and the resulting polymers can cause DNA to condense into compact structures. Such an approach is known in synthetic polymer chemistry as template polymerization. During this process, monomers (which are initially weakly associated with the template) are positioned along template's backbone, thereby promoting their polymerization. Weak electrostatic association of the nascent polymer and the template becomes stronger with chain growth of the polymer. Trubetskoy et al used two types of polymerization reactions to achieve DNA condensation: step polymerization and chain polymerization (V S Trubetskoy, V G Budker, L J Hanson, P M Slattum, J A Wolff, L E Hagstrom. Nucleic Acids Res. 26:4178–4185, 1998) U.S. Ser. No. 08/778,657, U.S. Ser. No. 09/000,692, U.S. Ser. No. 97/24089, U.S. Ser. No. 09/070299, and U.S. Ser. No. 09/464,871. Bis(2-aminoethyl)-1,3-propanediamine (AEPD), a tetramine with 2.5 positive charges per molecule at pH 8 was polymerized in the presence of plasmid DNA using cleavable disulfide amino-reactive cross-linkers dithiobis (succinimidyl propionate) and dimethyl-3,3'-dithiobispropionimidate. Both reactions yielded DNA/polymer complexes with significant retardation in agarose electrophoresis gels demonstrating significant binding and DNA condensation. Treatment of the polymerized complexes with 100 mM dithiothreitol (DTT) resulted in the pDNA returning to its normal supercoiled position following electrophoresis proving thus cleavage the backbone of the. The template dependent polymerization process was also tested using a 14 mer peptide encoding the nuclear localizing signal (NLS) of SV40 T antigen as a cationic "macromonomer". Other studies included pegylated comonomer (PEG-AEPD) into the reaction mixture and resulted in "worm"-like structures (as judged by transmission electron microscopy) that have previously been observed with DNA complexes formed from block co-polymers of polylysine and PEG (M A Wolfert, E H Schacht, V Toncheva, K Ulbrich, O Nazarova, L W Seymour. Human Gene Ther. 7:2123–2133, 1996). Blessing et al used bisthiol derivative of spermine and reaction of thiol-disulfide exchange to promote chain growth. The presence of DNA accelerated the polymerization reaction as measured the rate of disappearance of free thiols in the reaction mixture (T Blessing, J S Remy, J P Behr. J. Am. Chem. Soc. 120:8519–8520, 1998).

"Caging" of Polycation-Condensed DNA Particles

The stability of DNA nanoassemblies based on DNA condensation is generally low in vivo because they easily engage in polyion exchange reactions with strong polyanions. The process of exchange consists of two stages: 1) rapid formation of a triple DNA-polycation-polyanion complex, 2) slow substitution of one same-charge polyion with another. At equilibrium conditions, the whole process eventually results in formation of a new binary complex and an excess of a third polyion. The presence of low molecular weight salt can greatly accelerate such exchange reactions, which often result in complete disassembly of condensed DNA particles. Hence, it is desirable to obtain more colloidally stable structures where DNA would stay in its condensed form in complex with corresponding polycation independently of environment conditions.

The complete DNA condensation upon neutralization of only 90% of the polymer's phosphates results in the presence of unpaired positive charges in the DNA particles. If the polycation contains such reactive groups, such as primary amines, these unpaired positive charges may be modified. This modification allows practically limitless possibilities of modulating colloidal properties of DNA particles via chemical modifications of the complex. We have demonstrated the utility of such reactions using traditional DNA-poly-L-lysine (DNA/PLL) system reacted with the cleavable cross-linking reagent dimethyl-3,3'-dithiobispropionimidate (DTBP) which reacts with primary amino groups with formation of amidines (V S Trubetskoy, A Loomis, P M Slattum, J E Hagstrom, V G Budker, J A Wolff. Bioconjugate Chem. 10:624–628, 1999) U.S. Ser. No. 08/778,657, U.S. Ser. No. 09/000,692, U.S. Ser. No. 09/070299, and U.S. Ser. No. 09/464,871. Similar results were achieved with other polycations including poly(allylamine) and histone H1. The use of another bifucntional reagent, glutaraldehyde, has been described for stabilization of DNA complexes with cationic peptide CWK18 (R C Adam, K G Rice. J. Pharm. Sci. 739–746, 1999).

Recharging

The caging approach described above could lead to more colloidally stable DNA assemblies. However, this approach may not change the particle surface charge. Caging with bifunctional reagents, which preserve positive charge of amino group, keeps the particle positive. However, negative surface charge would be more desirable for many practical applications, i.e. in vivo delivery. The phenomenon of surface recharging is well known in colloid chemistry and is described in great detail for lyophobic/lyophilic systems (for example, silver halide hydrosols). Addition of polyion to a suspension of latex particles with oppositely-charged surface leads to the permanent absorption of this polyion on the surface and, upon reaching appropriate stoichiometry, changing the surface charge to opposite one. This whole process is salt dependent with flocculation to occur upon reaching the neutralization point.

We have demonstrated that similar layering of polyelectrolytes can be achieved on the surface of DNA/polycation particles (V S Trubetskoy, A Loomis, J E Hagstrom, V G Budker, J A Wolff. Nucleic Acids Res. 27:3090–3095, 1999). The principal DNA-polycation (DNA/pC) complex used in this study was DNA/PLL (1:3 charge ratio) formed in low salt 25 mM HEPES buffer and recharged with increasing amounts of various polyanions. The DNA particles were characterized after addition of a third polyion component to a DNA/polycation complex using a new DNA condensation assay (V S Trubetskoy, P M Slattum, J E Hagstrom, J A Wolff, V G Budker. Anal. Biochem. 267:309–313, 1999) and static light scattering. It has been found that certain polyanions such as poly(methacrylic acid) and poly(aspartic acid)

decondensed DNA in DNA/PLL complexes. Surprisingly, polyanions of lower charge density such as succinylated PLL and poly(glutamic acid), even when added in 20-fold charge excess to condensing polycation (PLL) did not decondense DNA in DNA/PLL (1:3) complexes. Further studies have found that displacement effects are salt-dependent. In addition, poly-L-glutamic acid but not the relatively weaker polyanion succinylated poly-L-lysine (SPLL) displaces DNA at higher sodium chloride concentrations. Measurement of ζ-potential of DNA/PLL particles during titration with SPLL revealed the change of particle surface charge at approximately the charge equivalency point. Thus, it can be concluded that addition of low charge density polyanion to the cationic DNA/PLL particles results in particle surface charge reversal while maintaining condensed DNA core intact.

The polyanion can be covalently attached to the polycation using a variety of chemical reactions without the use of crosslinkers. The polyanion can contain reactive groups that covalently attach to groups on the polycation. A preferable situation includes formation of a specific complex between a polyanion and a polycation, leaving the polyion and the polyampholyte to non-covalently interact electrostatically. The utility of such complexes includes enhanced colloid stability in serum and in high salt solutions and delivery of polyion (DNA) to hepatocytes in vivo upon intravenous administration.

DETAILED DESCRIPTION

Figure 1:
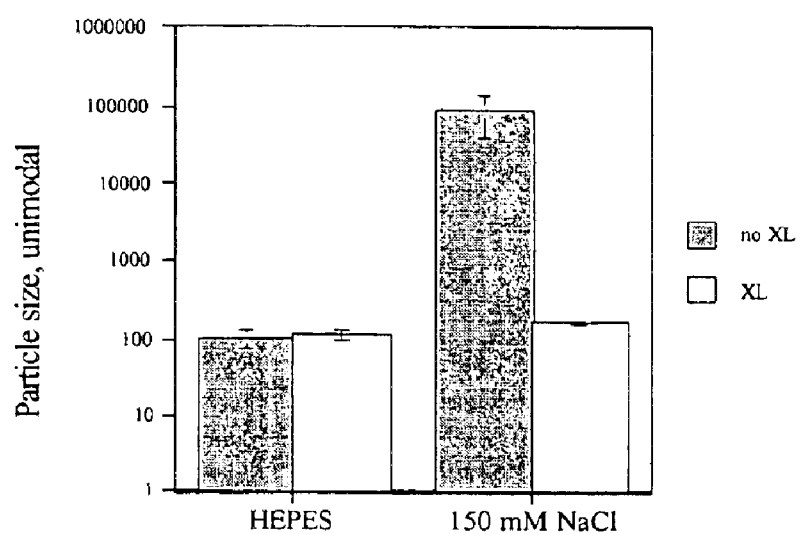
FIG. 1 illustrates the salt stability of cross-linked and non-crosslinked DNA/PLL/SPLL (1:3:10) particles.

Template polymerization has been defined as the following (van de Grampel, H. T., Tan, Y. Y. and Challa, G. Macromolecules 23, 5209–5216, 1990):

"Template polymerizations can be defined as polymerizations in which polymer chains are able to grow along template macromolecules for the greater part of their lifetime. Such a mode of propagation can be achieved through the existence of cooperative interactions between the growing chain and the template chain and usually leads to the formation of an interpolymer complex. In general, a well-chosen template is able to affect the rate of polymerization as well as the molecular weight and microstructure of the formed polymer (daughter polymer). The concepts of template polymerization were described by Ballard and Bamford with the ring opening polymerization of the N-carboxyanhydride of DL-phenylalanine on a polysarcosine template. Since then, many other systems involving radical and nonradical initiation of vinyl monomers have been studied in which one or more template effects, arising from this peculiar propagation mode, were identified. A number of radical-initiated template polymerizations have been studied, employing water as solvent".

The main features of template polymerization are:
1. Complex formation takes place between polymers
2. The rate of polymerization increases as the concentration of template increases. (Fujimori, K., (1979) Makromol. Chem. 180, 1743)
3. The structure and conformational features of the template are reflected in the corresponding daughter polymer.

In template polymerization, propagation of new polymer chain occurs predominantly along the template, a macromolecular chain, through specific cooperative interaction. The nature of interaction can be electrostatic, H-bonding, charge-transfer, and Van der Waals forces in combination with steriochemical matching. The presence of template usually affects various polymerization characteristics as well as the microstructure of the polymer formed. The mechanism of template polymerization depends on the degree of monomer adsorption. Two extreme cases can be discerned: the adsorption equilibrium coefficient for monomer, $KM=\bullet$ (type 1) and $KM=0$ (type 2). In type 1 ("zip" reaction) monomer is fully adsorbed onto all template sites and the polymerization occurs only on template. As the KM constant becomes smaller, template propagation increasingly proceeds via reaction monomers from the surrounding solution at the expense of reaction with adjacently adsorbed monomer. When $KM=0$ (type 2) only non-adsorbed monomer is present and the template macromolecules are completely solvated by solvents instead of the monomers. A prerequisite for template propagation under this condition is the growing daughter oligomer, created in bulk solution, that then complexes with template. ("pick-up" reaction). The chain length below which no complexation takes place (critical chain length) is important for magnitude of the template effect. In fact, there is no sharp border between type 1 and type 2 polymerization's.

Several processes for using template polymerization for drug delivery are described. The daughter polymer could be the drug. In a preferred embodiment, the template is the drug (defined to include pharmaceuticals, therapeutic agents or biologically active substances). The process of using template polymerization for drug delivery comprises mixing the template with monomers and having a daughter polymer forming from the monomers. The mixture of template polymer and daughter polymer is then administered to a cell by putting the mixture in contact with a cell or near a cell. The mixture of template and daughter polymer could also be placed in a pharmaceutical formulation and vial for delivery to an animal. The template polymer could be a polyanion such as nucleic acid including DNA, RNA or an antisense sequence.

After template polymerization networks or additional networks can be added to the polymer. These could be used to cross-link the polymers. For example, the polymer could be cross-linked to put the template into a "cage". Also targeting groups could be added during the initial template polymerization stage or during subsequent polymerization steps.

Definitions:

Substructure

Substructure means the chemical structure of the compound and any compounds derived from that chemical structure from the replacement of one or more hydrogen atoms by any other atom or change in oxidation state. For example if the substructure is succinic anhydride, then methylsuccinic anhydride, 2,2-dimethylsuccinic anhydride, 3-oxabicyclo[3.1.0]hexane-2,4-dione, maleic anhydride, citriconic anhydride, and 2,3-dimethylmaleic anhydride have the same substructure.

Succinylated (Succinylation)

Succinylated (Succinylation) means the compound obtained from the chemical reaction of the amine with succinic anhydride. For example, succinylated poly-L-lysine means the product from the chemical reaction between poly-L-lysine and succinic anhydride.

Salt
A salt is any compound containing ionic bonds, that is bonds in which one or more electrons are transferred completely from one atom to another. Salts are ionic compounds that dissociate into cations and anions when dissolved in solution and thus increase the ionic strength of a solution.

Pharmaceutically Acceptable Salt
Pharmaceutically acceptable salt means both acid and base addition salts.

Pharmaceutically Acceptable Acid Addition Salt
A pharmaceutically acceptable acid addition salt is those salts which retain the biological effectiveness and properties of the free bases, and are not biologically or otherwise undesirable, and which are formed with inorganic acids such as hydrochloric acid, hydrobromic acis, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethansulfonic acid, p=toluenesulfonic acid, salicylic acid, trifluoroacetic acid, and the like.

Pharmaceutically Acceptable Base Addition Salt
A pharmaceutically acceptable base addition salt is those salts which retain the biological effectiveness and properties of the free acids, and are not biologically or otherwise undesirable. The salts are prepared from the addition of an inorganic base or an organic base to the free acid. Salts derived from inorganic bases include, but are not limited to, sodium, potassium, calcium, lithium, ammonium, magnesium, zinc, and aluminum salts and the like. Salts derived from organic bases include, but are not limited to salts of primary secondary, and tertiary amines, such as methylamine, triethylamine, and the like.

New Definitions for Lipid

Lipid
Any of a diverse group of organic compounds that are insoluble in water, but soluble in organic solvents such as chloroform and benzene. Lipids contain both hydrophobic and hydrophilic sections. Lipids is ment to include complex lipids, simple lipids, and synthetic lipids.

Complex Lipids
Complex lipids are the esters of fatty acids and include glycerides (fats and oils), glycolipids, phospholipids, and waxes.

Simple Lipids
Simple lipids include steroids and terpenes.

Synthetic Lipids
Synthetic lipids includes amides prepared from fatty acids wherin the carboxylic acid has been converted to the amide, synthetic variants of complex lipids in which one or more oxygen atoms has been substitutied by another heteroatom (such as Nitrogen or Sulfur), and derivatives of simple lipids in which additional hydrophilic groups have been chemically attached. Synthetic lipids may contain one or more labile group.

Fats
Fats are glycerol esters of long-chain carboxylic acids. Hydrolysis of fats yields glycerol and a carboxylic acid—a fatty acid. Fatty acids may be saturated or unsaturated (contain one or more double bonds).

Oils
Oils are esters of carboxylic acids or are glycerides of fatty acids.

Glycolipids
Glycolipids are sugar containing lipids. The sugars are typically galactose, glucose or inositol.

Phospholipids
Phospolipids are lipids having both a phosphate group and one or more fatty acids (as esters of the fatty acid). The phosphate group may be bound to one or more additional organic groups.

Wax
Waxes are any of various solid or semisolid substances generally being esters of fatty acids.

Fatty Acids
Fatty acids are considered the hydrolysis product of lipids (fats, waxes, and phosphoglycerides).

Hydrophobic Groups
Hydrophobic groups indicate in qualitative terms that the chemical moiety is water-avoiding. Typically, such chemical groups are not water soluble, and tend not to form hydrogen bonds.

Hydrophilic Groups
Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides, and groups containing amines, amides, alkoxy amides, carboxylic acids, sulfurs, or hydroxyls.

The examples describe properties of polyion/ polyampholyte complexes when polyampholyte is formed in the presence of polyion. Example 1 represents general procedures for the synthesis of PLL-SPLL polyampholyte in the presence of DNA using water-soluble carbodiimide. Example 2 teaches that the formation of PLL-SPLL polyampholyte in the presence of DNA increases the colloid stability of the DNA complex in physiological salt solutions. Example 3 states that the net charge of cross-linked DNA/ PLL/SPLL stays negative. Example 4 demonstrates enhanced colloid stability of DNA/polyampholyte complex in the presence of serum. Example 5 teaches about delivery of DNA/PLL-SPLL polyampholyte complex to hepatocytes in vivo. Example 6 is about the same with DNA/ polyallylamine-cysteine-polyacrylic acid-thioester polyampholyte.

EXAMPLE 1

General procedure for the formation of the polyampholyte in the presence of DNA. (Crosslinking of polycation and polyanion layers on the DNA/PLL/SPLL particles using 1[3-(dimethylamino)propyl]-3-ethyl carbodiimide (EDC) and sulfo-N-hydroxysuccinmide (SNHS). Plasmid DNA (pCILuc) and PLL (M.w. 46 kDa) were mixed in a charge ratio 1:3 (100 ug and 190 ug respectively in 0.5 ml of 20 mM MES, pH 6.5. Succinylated PLL (SPLL) was activated with EDC/SNHS in 50 ul of unbuffered solution at pH 5.0 for 10 min (690 ug SPLL, 1.4 mg EDC, 700 ug SNHS). Then the DNA/PLL complex and activated SPLL were mixed (DNA:PLL:SPLL charge ratio 1:3:10) and the mixture was incubated overnight at room temperature.

EXAMPLE 2

Formation of PLL-SPLL Polyampholyte in the Presence of DNA Increases the Colloid Stability in Physiological Salt Solutions.

In this example the colloid stability of DNA/ polyampholyte particles obtained in Example 1 and control DNA/PLL/SPLL complexes were compared using quasielastic light scattering. Control DNA/PLL/SPLL complexes were prepared using the same charge ratios (1:3:10) as DNA/polyampholyte complex in Example 1 but without EDC/SNHS activation (no polyampholyte was formed). The complexes were sized in 10 mM HEPES, pH 7.5 or HEPES buffered saline (20 ug DNA/ml) using Zeta Plus Particle Size Analyzer (Brookhaven Instruments Corp.). Polyampholyte complexes demonstrate more resistance to aggregation in NaCl-containing solutions as compared to control non-covalent complexes (FIG. 1, XL stands for cross-linking).

EXAMPLE 3
Surface Charge of DNA Complexes Obtained by Formation of PLL-SPLL Polyampholyte in the Presence of DNA.

Figure 2:
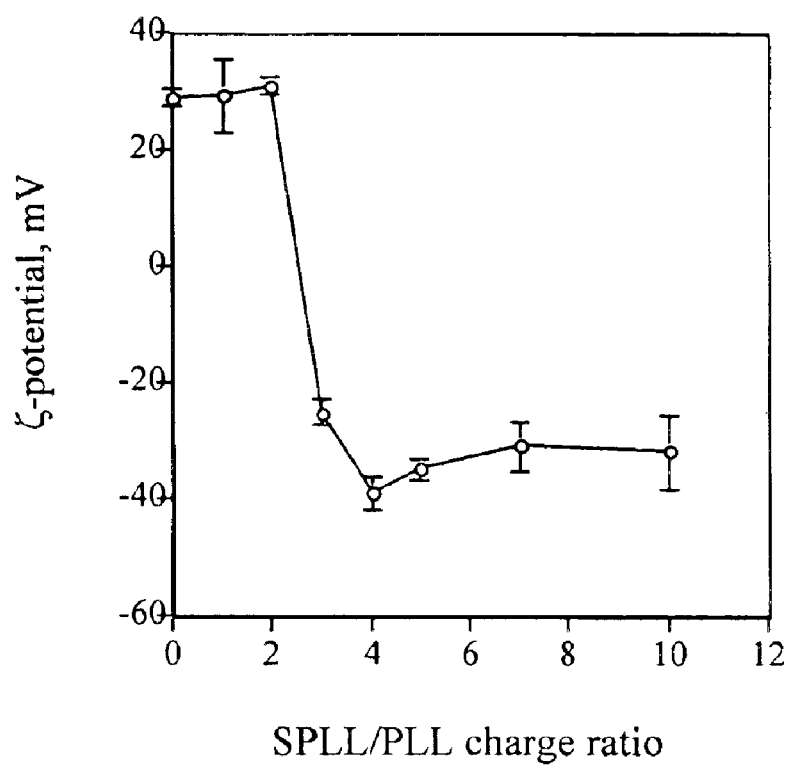
FIG. 2 illustrates the effect of amount of activated SPLL on the surface charge of DNA/PLL complexes.

The series of complexes were prepared as described in Example 1 except various amounts of activated SPLL were added to DNA/PLL (1:3) complex. Zeta potential was measured in 10 mM HEPES, pH 7.5 at DNA concentration of 20 ug/ml using Zeta Plus instrument. The results clearly indicate charge reversal when sufficient amounts of activated SPLL are added to form polyampholyte (FIG. 2).

EXAMPLE 4
Crosslinking of Polycation and Polyanion Layers on the DNA-Containing Particles Increases Their Stability in Serum and on the Cell Surface.

Negatively charged (recharged) particles of condensed DNA can possess the same physico-chemical properties as positively charged (non-recharged) ones. This includes flocculation in high salt solutions (including physiologic concentration). We found that chemical cross-linking of cationic and anionic layers of the DNA particles can substantially improve stability of the particles in serum as well as on the cell surface. Table 2 shows the time course of unimodal particle size of DNA/PLL/SPLL crosslinked and non-crosslinked particles in 80% bovine serum as determined by dynamic light scattering.

Table 2. Particle sizing of DNA/PLL/SPLL crosslinked and non-crosslinked complexes in 80% serum.

| Time, min crosslinking | size (nm) | no crosslinking | size (nm) |
| --- | --- | --- | --- |
| 0 | 153 | | 104 |
| 15 | 154 | | 105 |
| 60 | 171 | | 108 |
| 200 | 246 | | 115 |

Crosslinked particles essentially do not change their size in 200 min at room temperature while non-crosslinked control flocculates rapidly. Crosslinking with cleavable reagents might help to overcome an inactivity problem. The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines, acyl hydrazones, and Schiff bases.

EXAMPLE 5
Hepatocytes Delivery of Cross-Linked Tertiary DNA/PLL/SPLL Complexes by Tail Vein 10 Injection.
Materials:

Plasmid DNA (pCILuc) were labeled with Cy3 LableIT (Mirus Corporation, Madison Wis.).

Labeled DNA were typically dissolved in water at concentrations ranged from 1.5–2 mg/ml. 15

Poly-L-Lysine, PLL (MW 31 kDa), dissolved in water at 10 mg/ml was purchased from Sigma Chemicals (St. Louis, Mo.). Succinylated PLL (SPLL) was prepared as previously described and dissolved in water at 20 mg/ml.

DNA/PLL/SPLL cross-linked tertiary complexes were formed at a charge ratio of 1:3:10 as follows for a single injection: SPLL (345 ug in 50 ul of 20 mM MES, pH 5) were activated with the addition of 292 ug of 5 EDC followed by 583 ug of sulfo-NHS, both were dissolved in H2O at 100 mg/1.2 ml, and incubated for 10 min. At the end of the activation period, 50 ug of cy3-labeled DNA in 100 ul of 20 mM MES, pH 6.5 was added to 95 ug of PLL in 100 ul of 20 mM MES, pH 6.5 and mixed immediately. The condensed DNA/PLL complexes were added immediately to the activated SPLL solution and mixed thoroughly. The cross-linked particles were allowed to incubate at room temperature for at least 2 hr before in-vivo injections. Typically, majority of the particles size ranged from 60–200 nm with an average size around 130 nm and a Zeta-potential of −40 mV. Salt and serum stability of particles were evaluated by particles size changes over time in the presence of physiologic salt solution or serum. The cross-linked particles solution containing 50 ug of Cy3-DNA in 250 ul were injected into a mouse through the tail vein. After 3 hrs, the animal was sacrificed, liver samples were submerged in HistoPrep (Fisher Scientific) and snapped frozen in liquid nitrogen. Frozen liver sections, 4–5 um thick, were prepared and were counter stained sequentially for 20 min each by 10 nm Sytox green (Molecular Probe) in PBS for cell nuclei and 15 ng/ml of Alexa 488 phalloidin (Molecular Probe) in PBS for actin filaments. Stained slides were analyzed for hepatocytes uptake of Cy3-DNA containing particles using a Zeiss laser scanning confocal microscope. FIG. 1 shows the fluorescence signals from 10 consecutive confocal planes superimposed to form one image, each plane was 0.45 um thick. With the average size of a mouse hepatocyte around 25–30 um thick, the composite image roughly represent ¼ of total signals per hepatocytes. It showed that each cell contained 20–40 punctate signals. Each punctate signal may represent endosomes at various stages of the pathway and may contain one or more DNA containing particles. Hepatocytes were distinguishable by their larger size in comparison to other cells and bi-nucleated for a large percentage of the population. A few of the hepatocytes were indicated by (H). A large number of particles were also found in Kuppfer and endothelial cells. These sinusoidal cells were smaller in size, possessed very little cytoplasm space and were indicted by (S). Red=DNA containing tertiary complex. Green=cell nuclei and actin filaments which were localized primarily along the cell surface and with the strongest signal along bile canaliculi.

EXAMPLE 6
Hepatocytes Delivery of DNA/Polyallylamine-Cysteine/Polyacrylic Acid-Thioester Complexes
Materials:

Synthesis of polyallylamine-cysteine (pAllylamine-cys) conjugate: N,N'-bis(t-BOC)-L-cystine (37 mg, 0.08 mmol) was dissolved in 5 mL methylene chloride to this was added N-10 hydroxysuccinimide (21 mg, 2.2 eq) and dicyclohexylcarbodiimide (37 mg, 2.2 eq). The solution was allowed to stir overnight at room temperature. The dicyclohexylurea was removed by filtering the solution through a cotton plug in a Pasteur pipette. The succinimidyl ester was then added, with rapid stirring, to a solution of polyallylamine hydrochloride MW 50,000 (10 mg, 0.8 eq) that had been dissolved in a solution of methanol (20 mL) and 15 diisopropylethylamine (0.5 mL). After one hour, the solvents were removed by rotary evaporation. The white solid was then dissolved in trifluoroacetic acid (5 mL), triisopropylsilane (0.25 mL), and water (0.25 mL). The two hours, the solvents were removed by rotary evaporation. The resulting solid was then dissolved in water (25 mL) and the pH was adjusted to 9 by the addition of potassium carbonate. To this solution was added β-mercaptoethanol (1 mL). After two hours, the pH was adjusted to 2 by the addition of hydrochloride and the solution was placed into dialysis tubing (MWC 12,000) and dialyzed against 2 L of water that was adjusted to pH 2 with addition of hydrochloric acid. The dialysis solution was changed four times over 48 hours. After dialysis the solution contained 1.3 mg/mL polyallylamine, which is 14 mM of amine functional groups. Analysis of the thiol content of the solution by reaction with 5,5'-dithiobis(2-nitrobenzoic acid) in pH 7.5 100 mM phosphate buffer and quantification by comparison to solutions containing a known amount of β-mercaptoethanol revealed 2.7 mM of thiol functional groups, an 18% modification of all functional groups. Synthesis of polyacrylic acid thioester (pAA-thioester): To a solution of mercaptoacetic acid (1 mL) in 10 mL methylene chloride was added polyacryloyl chloride MW 10,000 (100 mg). After 30 minutes, the methylene chloride was removed by rotary evaporation and the•36 resulting oil was dissolved in 20 mL water and dialyzed against 2 L water. The dialysis solution was changed four times over a 72 hour period. The amount of thioester was quantified by measuring the absorbance of the thioester at 230 nm using the extinction coefficient of 3,800 M−1 cm−1 (Anal. Biochem. 1985, 150, 121) and was determined to be at 80% modification of all functional groups. Complexes for injection were formulated in 250 ul of 5 mM HEPES buffer, pH 8. For a single injection, 20 ug of pAllylamine-cys was added to 10 ug of Cy3-DNA. Polyacrylic acid thioester (60 ug) was then added to the condensed complex and let incubate overnight at 4° C.

Amide bonds were formed as interactions occurred between the cysteine groups and the thioester groups. These cross-linked particles had an average diameter of 94 nm in size and a Zeta-potential of −40 mV. Particle stability were evaulated by changes of particles size in the presence of physiologic salt and serum. Injection of complexes and analysis for hepatocyte delivery were essentially the same as described in example 1. FIG. 2 shows the delivery of Cy3-DNA/pAllyamine-cys/pAA-thioester particles, 1 to particles per hepatocytes, to at least 60% of the hepatocytes. Considering the lower concentration of DNA injected, the efficiency of hepatocytes delivery was comparable to that of Cy3-DNA/PLL/SPLL complexes. Similar to Cy3-DNA/PLL/SPLL complexes, sinusoidal cells (mostly endothelial and Kupffer cells) also contained a large number of particles. Red=DNA containing complexes. Green=cell nuclei and actin filaments. This example represent another method of cross-linking to formulate liver targetable negatively charged particles.

We claim:

1. A process for enhancing delivery of a polyion to a cell, comprising: forming a polyampholyte having a net charge, in the presence of a polyion; and, delivering the complex into a cell.

2. The process of claim 1 wherein the polyampholyte comprises a polycation selected from group consisting of (but not limited to) poly-L-lysine, poly-D-lysine, poly-L,D-lysine, polyethylenimine, polyallylamine, poly-L-ornithine, poly-D-ornithine, poly-L,D-ornithine, polyvinylamine, natural cationic protiens, synthetic cationic protiens, synthetic cationic peptides and synthetic polymers containing monomers with amines selected from but not limited to alkylamine, aryl amine, aralkylamine, imidazole, pyridine, and piperazine, pyrazine, pyrimidine, oxazoline, oxazole, oxazolidine. cationic polyvinylethers and their cationic copolymers.

3. The process of claim 1 wherein the polyampholyte comprises a polyanion.

4. The process of claim 3 wherein the polyanion comprises a molecule selected from the group consisting of poly-L-aspartic acid, poly-D-aspartic acid, poly-L,D-aspartic acid, polyacrylic acid, poly-L-glutamic acid, poly-D-glutamic acid, poly-L,D-glutamic acid, succinylated poly-L-lysine, succinylated poly-D-lysine, succinylated poly-L,D-lysine, succinylated polyethylenimine, succinylated polyallylamine, succinylated poly-L-ornithine, succinylated poly-D-ornithine, succinylated poly-L,D-ornithine, succinylated polyvinylamine, polymethacrylic acid, dextran sulfate, heparin, hyaluronic acid, DNA, RNA, natural anionic proteins, synthetic anionic proteins, synthetic anionic peptides, and synthetic polymers.

5. The process of claim 3 wherein the polyanion comprises a molecule selected from the group consisting of pegylated derivatives, pegylated derivatives carrying specific ligands, block copolymers, graft copolymers and hydrophilic polymers.

6. The process of claim 1 wherein the polyampholyte is delivered to a cell in vivo.

7. A complex for delivering a polyion to a cell, comprising: a polyion; and, a polyampholyte having a net charge.

8. The complex of claim 7 wherein the polyampholyte comprises a polycation.

9. The complex of claim 8 wherein the polycation is selected from group consisting of PLL and PEI.

10. The complex of claim 7 wherein the polyampholyte comprises a polyanion.

11. The complex of claim 10 wherein the polyanion comprises a molecule selected from the group consisting of succinylated PLL, succinylated PEI, polyglutamic acid, polyaspartic acid, polyacrylic acid, polymethacrylic acid, dextran sulfate, heparin, hyaluronic acid, DNA, RNA, and negatively charged proteins.

12. The complex of claim 11 wherein the polyanion comprises a molecule selected from the group consisting of pegylated derivatives, pegylated derivatives carrying specific ligands, block copolymers, graft copolymers and hydrophilic polymers.

13. A process for extravasation of a complex, comprising: forming a complex of polyion and polyampholyte having a net charge; and, inserting the complex into a vessel; delivering the complex to an extravascular space.

14. The complex of claim 13 wherein the polyampholyte comprises a polycation which is selected from group consisting of PLL and PEI.

15. The complex of claim 13 wherein the polyampholyte comprises a polyanion selected from the group consisting of succinylated PLL, succinylated PEI, polyglutamic acid, polyaspartic acid, polyacrylic acid, polymethacrylic acid, dextran sulfate, heparin, hyaluronic acid, DNA, RNA, and negatively charged proteins.

16. The complex of claim 15 wherein the negatively charged polyion comprises a molecule selected from the group consisting of pegylated derivatives, pegylated derivatives carrying specific ligands, block copolymers, graft copolymers and hydrophilic polymers.

* * * * *